United States Patent [19]
Ely et al.

[11] Patent Number: 5,717,148
[45] Date of Patent: Feb. 10, 1998

[54] ANALYSIS INSTRUMENT HAVING CARRIER WITH LIQUID RECEIVING WELLS

[75] Inventors: Keith Aldan Ely, Kennett Square, Pa.; Timothy Patrick Evers, Wilmington, Del.; Robert Eric Bernstine, Chesapeake City, Md.

[73] Assignee: Dade International Inc., Deerfield, Ill.

[21] Appl. No.: 592,774

[22] Filed: Jan. 26, 1996

Related U.S. Application Data

[63] Continuation of Ser. No. 276,186, Dec. 1, 1994, abandoned.

[51] Int. Cl.⁶ .................................................. G01N 35/00
[52] U.S. Cl. .............................. 73/864.21; 422/63
[58] Field of Search .................. 73/864.21, 863–865; 422/63, 64

[56] References Cited

U.S. PATENT DOCUMENTS

| | | | |
|---|---|---|---|
| 3,504,376 | 3/1970 | Bednar et al. | 23/230 |
| 3,552,441 | 1/1971 | Luhleich | 73/864.86 X |
| 3,748,911 | 7/1973 | Rousselet et al. | 73/423 |
| 4,451,433 | 5/1984 | Yamashita et al. | 422/63 |
| 4,577,514 | 3/1986 | Bradley et al. | 73/863 |
| 4,598,596 | 7/1986 | Wiseman et al. | 73/864 |
| 4,622,457 | 11/1986 | Bradley et al. | 235/464 |
| 4,664,885 | 5/1987 | Minekane et al. | 422/65 |
| 4,699,766 | 10/1987 | Yamashita | 422/64 |
| 4,721,137 | 1/1988 | Muller | 141/65 |
| 4,729,876 | 3/1988 | Hennessy et al. | 422/103 |
| 4,756,201 | 7/1988 | Uffenheimer | 73/864 |
| 4,761,268 | 8/1988 | Andersen et al. | 422/72 |
| 4,774,055 | 9/1988 | Wakatake et al. | 422/64 |
| 4,808,380 | 2/1989 | Minekane | 422/64 |
| 4,834,944 | 5/1989 | Wakatake | 422/64 |
| 4,836,038 | 6/1989 | Baldwyn | 73/864.21 |
| 4,844,868 | 7/1989 | Rokugawa | 422/64 |
| 4,906,433 | 3/1990 | Minekane | 422/64 |
| 4,908,186 | 3/1990 | Sakamaki | 422/64 |
| 4,951,512 | 8/1990 | Mazza et al. | 73/861 |
| 5,080,864 | 1/1992 | Shaw | 422/62 |
| 5,084,242 | 1/1992 | Sakuma et al. | 422/100 |
| 5,104,808 | 4/1992 | Laska et al. | 436/48 |
| 5,128,103 | 7/1992 | Wang et al. | 422/64 |
| 5,201,232 | 4/1993 | Uffenheimer | 73/864 |
| 5,209,903 | 5/1993 | Kanamori et al. | 422/65 |
| 5,212,094 | 5/1993 | Ogawa | 436/47 |
| 5,216,926 | 6/1993 | Lipscomb . | |
| 5,240,679 | 8/1993 | Stettler | 422/67 |
| 5,270,211 | 12/1993 | Kelln et al. | 436/43 |
| 5,296,911 | 3/1994 | Wayrauch et al. . | |
| 5,358,691 | 10/1994 | Clark et al. | 422/64 |
| 5,424,212 | 6/1995 | Pinsl-Ober et al. | 436/50 |
| 5,434,083 | 7/1995 | Mitsumaki et al. | 436/48 |
| 5,482,861 | 1/1996 | Clark et al. | 422/63 |

FOREIGN PATENT DOCUMENTS

| | | |
|---|---|---|
| 0 252 631 A2 | 1/1988 | European Pat. Off. . |
| 0316766 | 11/1988 | European Pat. Off. . |
| 3839080 | 11/1988 | Germany . |

*Primary Examiner*—Hezron E. Williams
*Assistant Examiner*—Jay L. Politzer
*Attorney, Agent, or Firm*—Leland K. Jordan

[57] ABSTRACT

An analysis instrument includes a container support (12), a carrier (24) having a plurality of liquid receiving wells (24W), a gross probe (40) movable along a locus of action (42) and a fine probe (50), the fine probe (50) being movable along a locus of action (52). In addition, various analysis, treatment and/or handling devices are also disposed at predetermined operating positions arranged along the loci of action (42, 52). Both the gross probe 40 and the fine probe 50 are each independently movable along their respective loci of action 42, 52 among one or more various extracting position(s) and one or more various dispensing position(s) to which either the support (12) and/or the carrier (24) may be moved, and/or among various operating position(s).

5 Claims, 1 Drawing Sheet

FIGURE

ANALYSIS INSTRUMENT HAVING CARRIER WITH LIQUID RECEIVING WELLS

This is a continuation of application Ser. No. 08/276/186 filed Jul. 15, 1959, now abandoned.

BACKGROUND OF THE INVENTION

CROSS-REFERENCE TO RELATED APPLICATION

Subject matter disclosed and claimed herein is disclosed in copending application of Ely et al. titled Liquid Extraction Apparatus, filed contemporaneously herewith and accorded Ser. No. 08/516,593.

FIELD OF THE INVENTION

The present invention relates to a chemical analysis instrument, and in particular, to a chemical analysis instrument wherein both a gross probe and a fine probe are movable along independent loci of action among various analysis, treatment and/or other liquid handling devices.

DESCRIPTION OF THE PRIOR ART

In the field of automatic analytical and diagnostic analysis there is a premium placed on the ability of an instrument to exhibit a high throughput, that is, the ability to process a relatively large number of patient samples in a given period of time. Samples which are non-toxic and non-hazardous are carried in open containers, such as open test tubes. However, to avoid exposing operators to contact with potentially hazardous serum and other unsafe materials, it may be desirable to carry other samples in containers which are capped, i.e., the top of the container is closed by a rubber stopper or other suitable cap mechanism. Exemplary of a closed container is that container sold by Becton-Dickinson Company, East Rutherford, N.J., under the trademark Vacutainer®. Such a container is evacuated to facilitate aspiration of a whole blood sample from a patient.

It is necessary in the context of automated high throughput analysis instrument to be able to provide a precise amount of an extracted sample from either an open or closed container. An open container presents no obstacle to the withdrawal of a precisely metered volume of a sample for analysis. Complications are encountered with the use of an evacuated capped container. One complication is the need of a relatively more substantial sample probe to penetrate the rubber stopper. Such a sampling probe may not be able to meter precisely relatively small amounts of liquid. A further complication is the difficulty to extract accurately a predetermined volume of sample due to air pressure within the tube. The tube may be vented before a sample may be withdrawn.

In addition to being able to sample from both open and closed tubes, to effectuate high throughput it is imperative that any pre-analysis treatment of the extracted sample be handled in an efficient manner. Such pretreatment may include dilution or stabilization. Thereafter, the sample must be efficiently routed to the appropriate analysis device(s) for appropriate chemical analysis. These steps should be performed without the necessity of any operator intervention and with apparatus having the minimum necessary mechanical complexity.

In view of the foregoing it is believed advantageous to provide an analysis instrument having such flexibility of operation as to permit sample extracted from either capped or open containers to be dispensed to any one of a plurality of predetermined locations, including one or more analysis device(s), with or without the benefit or dilution of other forms of pretreatment.

U.S. Pat. No. 4,721,137 (Mueller) has a puncture tube which first penetrates the stopper and a sampling probe which is separate from the puncture tool to extract a liquid sample. U.S. Pat. No. 4,577,514 and U.S. Pat. No. 4,622,475 (both to Bradley et al.) both have a puncture tube which first penetrates the stopper and a separate sampling probe which is movable concentrically within the puncture tube to extract a liquid sample. U.S. Pat. No. 4,951,512 (Mazza et al.) uses a puncture tube to create an opening in the closed cap of the container and either takes a sample through this puncture tube or inserts a separate probe through the puncture tube to measure properties of the sample.

U.S. Pat. Nos. 4,756,201 and 5,201,232 (both to Uffenheimer) both disclose an apparatus that extracts samples from open and closed containers. However, these apparatus both require that a closed tube be segregated by an operator and positioned upside-down for sampling to occur. This renders automation difficult since open tubes must be positioned apart from and handled differently from the closed tubes.

U.S. Pat. No. 5,216,926 (Lipscomb) provides an apparatus for sampling from both open and closed containers. The disclosed apparatus includes a single transfer vessel to contain extracted samples.

U.S. Pat. No. 4,774,055 (Wakatake et al.) discloses an open tube analysis instrument in which three separate pipettes are provided. One pipette extracts sample from a sample support table and deposits it in a reaction chamber disposed on a rotatable table. The other two pipettes dispense reagent into the reaction chamber. The rotatable table carrying the sample chamber is coaxial with the sample support table.

SUMMARY OF THE INVENTION

An analysis instrument 10 in accordance with the present invention includes a support (12) for supporting closed or open sample liquid containers ($T_c$, $T_o$), a gross probe (40), a fine probe (50), and a carrier (24) having a plurality of liquid receiving wells (24W). The probes (40, 50) are each able either to dispense or to draw (extract) a volume of liquid sample or other liquid. The support (12) is movable to dispose any one of the containers ($T_c$, $T_o$) at either a gross probe sample extracting position (18I, 18E) or at a fine probe sample extracting position (20I, 20E), while the carrier (24) is movable to dispose any one of the plurality of liquid receiving wells (24W) therein at either a gross probe dispensing position (28I, 28E) or a fine probe operating position (30I, 30E).

The gross probe (40) is movable along a locus of action (42) between the gross probe sample extracting position (18I, 18E) and the gross probe dispensing position (28I, 28E). In the gross probe sample extracting position (18I, 18E) the gross probe (40) is able to draw thereinto liquid sample from either a closed or an open container ($T_c$, $T_o$) there disposed by the support (12). In the gross probe dispensing position (28I, 28E) the gross probe is able to dispense previously withdrawn liquid into a well (24W) there disposed by the carrier (24).

The fine probe (50) is movable along a locus of action (52) between a fine probe sample extracting position (20I, 20E) and a fine probe operating position (30I, 30E). In the fine probe sample extracting position (20I, 20E) the fine probe (50) is able to draw thereinto liquid sample from an open container ($T_o$) there disposed by the support (12), while in the fine probe operating position (30I, 30E) the fine probe is able either to dispense therefrom previously withdrawn liquid or to draw thereinto liquid, both from a well (24W) there disposed by the carrier (24).

An analysis device (56) may be disposed at a second dispensing position (62) located along the locus of action (42) of the gross probe (40), while a second analysis device (70) is disposed at a position (74) located along the locus of action (52) of the fine probe (50). Additionally, a reservoir (58) holding a sample treatment liquid may be disposed at a second extracting position (64) located along the locus of action (42) of the gross probe (40) and a reservoir (72) holding a sample treatment liquid may be disposed at a second extracting position (76) located along the locus of action (52) of the fine probe (50).

In general, the various sample analysis, sample treatment and/or sample handling devices are arranged so that both the gross probe (40) and the fine probe (50) are each independently movable along their respective loci of action (42, 52) among one or more various extracting position(s), one or more various dispensing position(s), and/or one or more various operating position(s) (i.e., positions where either extracting and/or dispensing may occur), thus imparting a flexibility of operation to the instrument (10) so configured.

BRIEF DESCRIPTION OF THE DRAWINGS

The invention will be more fully understood from the following detailed description, taken in connection with the accompanying drawing, which forms part of this application, and in which.

DETAILED DESCRIPTION OF THE INVENTION

Figure 1:
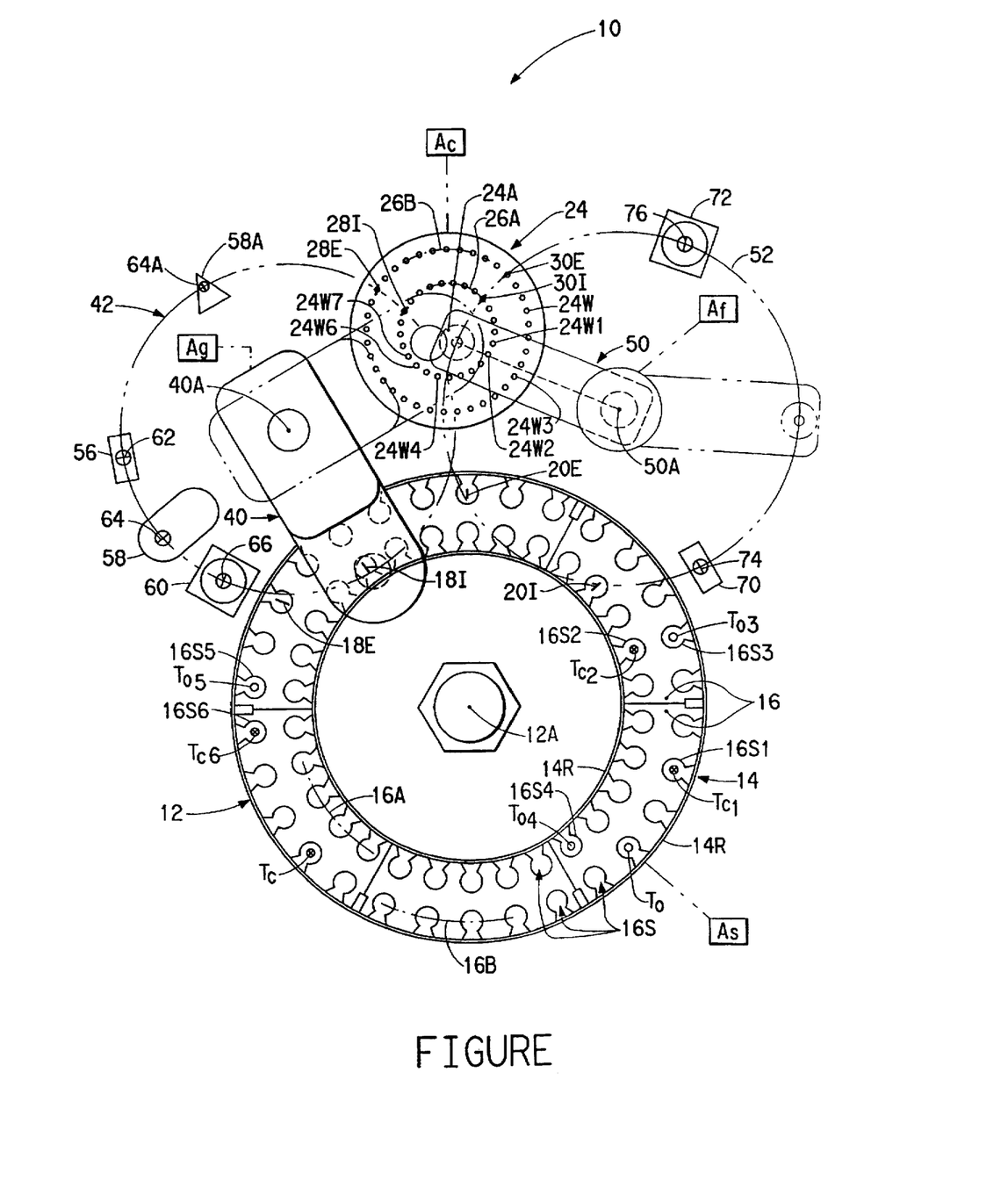
the sole FIGURE is a schematic plan view of a portion of an analysis instrument in accordance with the present invention wherein the various sample analysis, sample handling and sample treatment devices are relatively positioned in a predetermined arrangement.

The FIGURE schematically illustrates a portion of an analysis instrument, generally indicated by the reference character 10, the various sample analysis, liquid handling, and sample treatment devices thereof being relatively positioned with respect to each other in a predetermined manner in accordance with the invention. Since the FIGURE is intended as a schematic illustration, details regarding particular structural details of the instrument, such as the instrument framework and housing, and the manner in which various of the devices are interconnected to their associated drive actuator, and overall operating controller, are omitted. However, these and other details should be readily apparent to those skilled in the art, especially in view of commercially available analysis instruments of the same general type. Exemplary of such commercially available instruments is the clinical chemistry system manufactured and sold by the Medical Products Division of E. I. du Pont de Nemours and Company under the trademark Dimension®.

The instrument 10 includes a sample container support 12 for supporting closed or open containers, each having a liquid therein. The liquid may be a sample of a patient's body liquid, a calibrator liquid, or a chemical reagent liquid. Several of the closed containers are generally indicated in various slots by the reference character $T_c$, while represen-tative open containers are generally indicated by the reference character $T_o$. The container support 12 is preferably implemented in the form of a generally circular wheel 12. The support 12 may be shaped other than circularly, if desired. The support 12 is preferably rotatably movable with respect to an axis 12A. It should be understood that the support 12 may, alternately, be movable in direction(s) other than rotatably. For example, the support 12 may be recti-linearly movable with respect to the axis 12A along one or more directions, some of which may be mutually perpen-dicular if desired. The wheel 12 includes an annular, hol-lowed rim 14 that is generally U-shaped in cross section bounded by radially inner and outer rails 14R.

A plurality of arcuately shaped sample trays 16 is received by rim 14. Each sample tray 16 is held radially in place by the rails 14R. Each tray 16 has one or more arcuate rows of sample container receiving slots, generally indicated by the reference character 16S. Each slot 16S is appropriately sized and configured to receive either an open container $T_o$ or a closed container $T_c$ therein. Each row of slots 16S in each segment 16 cooperates with the corresponding row of slots 16S in the angularly adjacent segment to define at least one annular array, but more preferably, both an inner and an outer concentric annular array of slots. The inner array of slots is indicated by the reference character 16A, while the outer array of slots is indicated by the character 16B. It should also be understood that the slots may be otherwise arrayed, as in a spiral pattern, and remain within the con-templation of this invention.

The container support 12 is operatively connected to a suitable actuator (diagrammatically indicated by the refer-ence character $A_s$) for effecting the desired movement thereof with respect to the axis 12A. Suitable for use as the actuator $A_s$ is an encoded stepper motor driven belt. In general, the support 12 is movable to dispose any one of the containers received within a slot 16S in the slot array to at least two predetermined sample extracting positions defined at predetermined spaced locations with respect to the axis 12A. More particularly, in the context of the double con-centric annular array arrangement of the slots in the sample container support 12 shown in the FIGURE, rotatable move-ment of the support 12 serves to position any container $T_c$ or, $T_o$ carried in a slot 16S in the inner concentric annular array 16A to at least either a first predetermined inner sample extracting position 18I or a second predetermined inner sample extracting position 20I. Similarly, movement of the support 12 by the actuator $A_s$ serves to position any con-tainer $T_c$ or, $T_o$ carried in a slot 16S in the outer concentric annular array 16B to at least either a first predetermined outer sample extracting position 18E or a second predeter-mined outer sample extracting position 20E. The sample extracting positions 18I, 18E, respectively, and the sample extracting positions 20I, 20E, respectively, are angularly offset from each other by predetermined angular distances.

If desired each tray 16 may have one or more arcuate row(s) of sample container receiving slots disposed between the radially inner and outer rows shown in the FIGURE. Such additional arcuate rows would cooperate to define additional intermediate concentric annular array(s) of slots. In accordance with this invention a pair of predetermined sample extracting positions is defined for each additional annular array. A slot in each additional annular array may be positioned at either sample extracting position in the pair by movement of the support 12.

In general, when a container $T_c$ or, $T_o$ in a slot 16S in any particular annular array (e.g., 16A, 16B) is positioned at either of the inner sample extracting positions 18I, 20I or at either of the outer sample extracting positions 18E, 20E corresponding to that array, the liquid therein is able to be withdrawn therefrom.

The instrument 10 also includes a carrier 24 having a plurality of liquid receiving wells 24W therein formed to define at least one generally annular array 26. However, more preferably, the carrier 24 has at least both an inner and an outer concentric annular array 26A, 26B, respectively, of wells 24W. Each well 24W is sized to accommodate at least a predetermined liquid volume, and thus defines a receptacle wherein sample liquid may be handled and treated. The carrier 24 is operatively connected to a suitable actuator (diagrammatically indicated by the reference character $A_c$,) similar to the actuator $A_s$,) whereby the carrier 24 is movable with respect to an axis 24A. The axis 24A is displaced from the axis 12A of the container support 12. Preferably the carrier 24 is rotatably moved with respect to the axis 24A. However, as in the case of the support 12, the carrier 24 may be otherwise movable, as in one or more rectilinear directions, some of which may be mutually perpendicular. In general the carrier 24 is movable with respect to the axis 24A to dispose any of the wells 24W at one or more predetermined positions. Preferably appropriate rotatable movement of the carrier 24 with respect to the axis 24A serves to dispose any one of the wells 24W in each annular array to at least two predetermined operating positions defined at predetermined spaced angular locations with respect to the axis 24A. It should also be noted that the wells 24W may also be otherwise arrayed, e.g., in a spiral pattern. Although shown as circular in shape in the FIGURE, it should be understood that the carrier 24 may exhibit any desired shape.

In connection with the apparatus illustrated in the FIGURE rotatable movement of the carrier 24 serves to position any well 24W disposed in the inner concentric circular array 26A to at least either a first predetermined inner operating position 28I or an angularly offset second predetermined inner operating position 30I. Similarly, movement of the carrier 24 by the actuator $A_c$ serves to position any well 24W disposed in the outer concentric circular array 26B to at least either a first predetermined outer operating position 28E or an angularly offset second predetermined outer operating position 30E. If desired the carrier 24 may have one or more additional annular array(s) of wells disposed between the radially inner and outer arrays of wells shown in the FIGURE. At least two predetermined operating positions are defined for a well in each additional annular array of wells. As will be developed when a well 24W is disposed at a given operating position a liquid may be either drawn therefrom (i.e., extracted therefrom) and/or dispensed thereinto.

The instrument 10 further includes sample handling devices in the form of a first, gross, probe 40 and a second, fine, probe 50. The gross probe 40 is operatively connected to an actuator (diagrammatically indicated by the reference character $A_g$) whereby the probe 40 is movable along a predetermined, preferably circular, locus 42 centered about an axis 40A. The axis 40A is spaced with respect to the axes 12A and 24A of the support 12 and the carrier 24, respectively. Again, preferably the actuator $A_g$ is implemented in the form of a belt driven by an encoded stepping motor. Similarly, the fine probe 50 is operatively connected to an actuator (diagrammatically indicated by the reference character $A_f$, similar to the actuator $A_g$) whereby the probe 50 is movable along a separate predetermined locus 52. The locus 52 is centered about an, axis 50A that is spaced with respect to the axes 12A and 24A of the support 12 and the carrier 24, respectively, and with respect to the axis 40A of the probe 40. The locus 52 of the fine probe 50 is also preferably generally circular in form.

The gross probe 40 may be implemented by any suitable liquid extracting arrangement so long as the probe 40 is able to draw (i.e., extract) liquid from either a closed or an open tube or other liquid reservoir or liquid receptacle. To satisfy the needs of the present invention the gross probe 40 is required only to be able to control in a relatively gross manner the volume of liquid able to be either drawn thereinto or dispensed therefrom. The term "relatively gross control" should be construed to mean liquid volume control to the order often microliters. Details of the preferred form of the liquid extraction apparatus used to implement the gross probe are disclosed and claimed in above referenced contemporaneously filed copending application, assigned to the assignee of this invention. On the other hand, the fine probe 50 is required to be able to draw or to dispense relatively finely metered amounts of liquid. The term "relatively finely metered" should be construed to mean liquid volume control to the order of tenths of microliters.

The locus 42 of the gross probe 40 contains the first predetermined inner sample extracting position 18I, the first predetermined outer sample extracting position 18E, the first predetermined inner operating position 28I, and the first predetermined outer operating position 28E. When positioned at either the inner sample extracting position 18I or the outer sample extracting position 18E the gross probe is able to draw thereinto liquid sample that is carried within either a closed container $T_c$ or an open container $T_o$ that is disposed by the support 12 at that sample extracting position. Moreover, when positioned at either the inner operating position 28I or the outer operating position 28E the gross probe is able either to dispense into the well 24W positioned at the position 28I, 28E liquid that has been previously drawn into the probe or to draw into the probe (i.e., extract from the well) liquid that is present in the well.

The locus 52 of the fine probe 50 contains the first predetermined inner sample extracting position 20I, the first predetermined outer sample extracting position 20E, the first predetermined inner operating position 30I, and the first predetermined outer operating position 30E. When positioned at either the inner sample extracting position 20I or the outer sample extracting position 20E the fine probe 50 is able to draw thereinto liquid sample that is carried within an open container $T_o$ that is disposed by the support 12 at that open sample extracting position. However, when positioned at either the inner operating position 30I or the outer operating position 30E the fine probe is able either to dispense into the well positioned at the position 30I, 30E liquid that has been previously drawn into the probe or to draw into the fine probe (i.e., extract from the well) liquid that is present in the well.

Various other liquid handling, sample analysis and/or sample treatment functional devices of the analysis instrument 10 may be positioned about the locus 42 defined by the movement of the gross probe 42. In the FIGURE three such representative additional devices 56, 58, 60 are respectively located at predetermined angular positions 62, 64, 66 along the locus 42. In general, each of these angular positions 62, 64, 66 defines an operating position at which the gross probe is able either to dispense liquid or to extract liquid. Of course, the precise function of the device 56, 58, 60 at each respective angular position 62, 64, 66 will serve to determine the primary action performed by the probe at a given location.

For example, the device 56 located at the angular position 62 is, in the preferred implementation of the instrument 10, an analysis device of the ion selective electrode (ISE) type. Suitable for use as the ion selective electrode analysis device is that device manufactured by the Medical Products division of E. I. du Pont de Nemours and Company as sold as part of the clinical chemistry system identified by the trademark Dimension®. This analysis device is disclosed in U.S. Pat. No. 5,284,568 issued on Feb. 8, 1994 and assigned to the assignee of the present invention. The primary action of the probe 40 at the analysis device 56 is the dispensation of liquid sample or treated sample from the probe into the analysis device. Accordingly, the angular location 62 serves to define a second dispensing position along the locus 42 at which the probe 40 may dispense liquid.

By way of further example, the device 58 located at the angular position 64 is, in the preferred implementation of the instrument 10, a liquid reservoir for either a treatment liquid, (e.g., a diluent liquid solution for diluting a patient sample or a chemical reagent for chemically treating the patient sample) or a wash station for cleaning the liquid handling probe. In the former case (diluent or reagent) the primary action of the probe 50 at the device 58 is extracting liquid from the reservoir into the probe. Accordingly, the angular location 62 would serve to define a second liquid extracting position along the locus 42 at which the probe may draw a liquid thereinto. Alternatively, in the latter case (i.e., a wash station) the device 58 disposed in the position 64 may be either a reservoir or a drain, dependent upon the form of probe wash utilized. If the wash liquid is disposed in a reservoir, then the primary actions of the probe 50 at the device 58 would include both dispensing liquid to and extracting liquid from the reservoir. However, if the wash liquid is pumped into and through the probe from a source (not shown) then the primary action of the probe 50 at the device 58 would be the dispensing of liquid into the drain. Thus at the wash location the probe 50 may either extract, dispense, or both, as appropriate.

It should be appreciated that if either a diluent or a reagent liquid solution is disposed in the reservoir 58, then it lies within the contemplation of the invention to dispose the wash solution in a second reservoir device 60 which may be disposed at the angular position 66. Since at a wash position the probe both dispenses and extracts, the angular position 66 would serve to define a third extracting position at which the probe 40 draws liquid thereinto. Furthermore, it should be understood that additional liquid handling, sample analysis and/or sample treatment functional devices, such as additional reservoir(s) for other chemical liquids may also be positioned at additional location(s) about the locus 42, e.g., a reservoir 58A at an angular position 64A may contain a liquid chemical reagent.

In similar fashion it should be understood that various additional functional devices of the analysis instrument 10 may be positioned about the locus 52 defined by the movement of the fine probe 50. In the FIGURE two such additional devices 70, 72 are respectively located at respective predetermined angular positions 74, 76 along the locus 52. In general, each of these angular positions 74, 76 defines an operating position at which the fine probe is able either to dispense liquid or to extract liquid. Of course, the precise function of the device 70, 72 at the respective angular position 74, 76 will serve to determine the primary action performed by the probe 50 at a given location.

For example, the device 70 located at the angular position 74 is, in the preferred implementation of the instrument 10, an analysis device of the photometric type. Suitable for use as the photometric analysis device is that manufactured and sold by the Medical Products division of E. I. du Pont de Nemours and Company as part of the clinical chemistry system identified by the trademark Dimension®. This photometric analysis is disclosed in U.S. Pat. No. 4,863,693 issued on Sep. 5, 1989 to G. W. Howell and assigned to the assignee of the present invention. The primary action of the probe 50 at the analysis device 70 is the dispensation of liquid from the probe into the analysis device. Accordingly, with respect to the fine probe 50, the angular location 74 serves to define a second dispensing position along the locus 52 at which the probe 50 may dispense liquid.

Further, the device 72 located at the angular position 76 is, in the preferred implementation of the instrument 10, a liquid reservoir, primarily for a wash solution. Noting that at a wash position the probe 50 both dispenses and extracts liquid, the angular position 76 serves to define a second liquid extracting position along the locus 52 of the probe 50. In keeping with the foregoing it should be appreciated that additional devices of various functionality may be additionally disposed at spaced angular positions along the locus 52.

In general, the foregoing should also make apparent that however the various analysis, treatment and/or handling devices are arranged, in accordance with the present invention both the probe 40 and the probe 50 are each independently movable along their respective loci of action 42, 52 among one or more various extracting position(s), one or more various dispensing position(s) and/or one or more various operating position(s) (i.e., both extracting and dispensing). The flexibility of operation imparted to an instrument 10 so configured may be made more clear from the following operational examples.

EXAMPLES

Three closed containers are positioned in slots 16S1, 16S2 and 16S6, the containers indicated by reference characters $T_{c1}$, $T_{c2}$ and $T_{c6}$, respectively. Three open containers are positioned in slots 16S3, 16S4 and 16S5, the containers indicated by reference characters $T_{o3}$, $T_{o4}$, $T_{o5}$, respectively. Slots 16S1 and 16S3 are located on the outer concentric circular array 16B. Slots 16S2 and 16S4 are located on the inner concentric circular array 16A, respectively. Slots 16S5 and 16S6 are located on the outer concentric circular array 16B. Various different analytical tests are to be performed upon the different sample fluids contained in the different closed and open containers $T_{c1}$, $T_{c2}$, $T_{o3}$, $T_{o4}$, $T_{o5}$, and $T_{o6}$, as described below:

Example 1

Analytical Test 1 in which a liquid sample is extracted from a closed container and provided to two separate analysis devices without pretreatment.

1. Support 12 is rotated by actuator $A_s$ to position slot 16S1 containing closed container $T_{c1}$ at a first predetermined outer sample extracting position 18E. Gross probe 40 is rotated by actuator $A_g$ to position gross probe 40 at the first predetermined outer sample extracting position 18E and is operated to extract a first predetermined sample volume from closed container $T_{c1}$. Gross probe 40 is withdrawn from the sample volume, operated to extract a volume of air and repositioned to extract a second predetermined sample volume from closed container $T_{c1}$, the volume of air separating the first and second predetermined sample volumes.

2. Carrier 24 is rotated by actuator $A_c$ to position well 26W1 in the inner concentric annular array of wells 26A at the first predetermined inner operating position 28L. Gross probe 40 is next rotated by actuator $A_g$ to position gross probe 40 at the first predetermined inner operating position 28I whereat the second predetermined sample volume taken previously from closed container $T_{c1}$ is disposed into well 24W1. Gross probe 40 is next rotated by actuator $A_g$ to position gross probe 40 at the second dispensing position located at angular position 62 along the locus 42 whereat the first predetermined sample volume taken previously from closed container $T_{c1}$ is disposed into an analysis instrument 56 located at the second dispensing position.

3. Carrier 24 is next rotated by actuator $A_c$ to position well 24W1 in the inner concentric annular array of wells 26A at the second predetermined inner operating position 30I. Fine probe 50 is rotated by actuator $A_f$ to position fine probe 50 at the second predetermined inner operating position 30I whereat the second predetermined sample volume taken previously from closed container $T_{c1}$ and disposed into well 26W1 by gross probe 40 is extracted therefrom. Fine probe 50 is next rotated by actuator $A_f$ to angular position 74 along the locus 52 whereat the second predetermined sample volume taken previously from closed container $T_{c1}$ is disposed by fine probe 50 into an analysis device 70 located at the second dispensing position.

Example 2

Analytical test 2 in which liquid sample is extracted from a closed container and provided to a first analysis device without pretreatment and is also provided to a second analysis device after a diluting pretreatment.

1. Support 12 is rotated by actuator $A_s$ to position slot 16S2 containing container $T_{c2}$ at the first predetermined inner sample extracting position 18I. Gross probe 40 is rotated by actuator $A_g$ to position gross probe 40 at the first predetermined inner sample extracting position 18I and is operated to extract a first predetermined sample volume from closed container $T_{c2}$. Gross probe 40 is withdrawn from the sample volume, operated to extract a volume of air and repositioned to extract a second predetermined sample volume from closed container $T_{c2}$, the volume of air separating the first and second predetermined sample volumes.

2. Carrier 24 is rotated by actuator $A_c$ to position well 24W2 in the inner concentric annular array of wells 26A at the first predetermined inner operating position 28I. Gross probe 40 is next rotated by actuator $A_g$ to position gross probe 40 at the first predetermined inner operating position 28I whereat the second predetermined sample volume taken previously from closed container $T_{c1}$ is disposed into well 26W2. Gross probe 40 is next rotated by actuator $A_g$ to position gross probe 40 at the second dispensing position located at angular position 62 along the locus 42 whereat the first predetermined sample volume taken previously from closed container $T_{c1}$ is disposed into an analysis instrument 56 located at the second dispensing position.

3. Gross probe 40 is next rotated by actuator $A_g$ to position gross probe 40 at angular position 66 along the locus 42 whereat a wash solution is disposed in the second device 60. Gross probe is operated to extract wash solution thereinto and subsequently to extract wash solution therefrom, a process that may be repeated sufficiently to cleanse gross probe 40.

4. Gross probe 40 is next rotated by actuator $A_g$ to position gross probe 40 at angular position 64 along the locus 42 whereat a dilution solution is disposed in the device 58. Gross probe 40 is next operated to extract a predetermined volume of dilution solution therefrom. Gross probe 40 is next rotated by actuator $A_g$ to position gross probe 40 at the first predetermined inner operating position 28I whereat the predetermined volume of dilution solution taken previously from device 58 is disposed into well 24W2.

5. Carrier 24 is next rotated by actuator $A_c$ to position well 24W2 in the inner concentric annular array of wells 26A at the second predetermined inner operating position 30I. Fine probe 50 is next rotated by actuator $A_f$ to position fine probe 50 at the second predetermined inner operating position 30I whereat the second predetermined sample volume taken previously from closed container $T_{c2}$ and the predetermined volume of dilution solution taken previously from device 58 and also disposed into well 24W2 is extracted therefrom. Fine probe 50 is next rotated by actuator $A_f$ to position fine probe 50 at the second operating position 30I whereat the second predetermined sample volume taken previously from closed container $T_{c2}$ and the predetermined volume of dilution solution taken previously from device 58 and also disposed into well 24W2 is disposed by fine probe 50 into an analysis device 70 located at the second dispensing position.

Example 3

Analytical Test 3 in which a liquid sample is extracted from an open container and provided to two separate analysis instruments without pretreatment.

1. Support 12 is rotated by actuator $A_s$ to position slot 16S3 containing open container $T_{o3}$ at the first predetermined outer sample extracting position 18E. Gross probe 40 is rotated by actuator $A_g$ to position gross probe 40 at the first predetermined outer sample extracting position 18E. Gross probe 40 is operated to extract a first predetermined sample volume from open container $T_{o3}$, is withdrawn from the liquid sample, operated to extract a volume of air, and repositioned into the liquid to extract a second predetermined sample volume from open container $T_{o3}$, the volume of air separating the first and second predetermined sample volumes.

2. Carrier 24 is rotated by actuator $A_c$ to position well 24W3 in the outer concentric annular array of wells 26B at the first predetermined outer operating position 28E. Gross probe 40 is next rotated by actuator $A_g$ to position gross probe 40 at the first predetermined outer operating position 28E whereat the second predetermined sample volume taken previously from open container $T_{o3}$ is disposed into well 24W3. Gross probe 40 is next rotated by actuator $A_g$ to position gross probe 40 at the second dispensing position located at angular position 62 along the locus 42 whereat the first predetermined sample volume taken previously from open container $T_{o3}$ is disposed into an analysis instrument 56 located at the second dispensing position.

3. Carrier 24 is next rotated by actuator $A_c$ to position well 24W3 in the outer concentric annular array of wells 26B at the second predetermined outer operating position 30E. Fine probe 50 is next rotated by actuator $A_f$ to position fine probe 50 at the second predetermined outer operating position 30E whereat the second predetermined sample volume taken previously from open container $T_{o3}$ and disposed into well 24W3 by gorss probe 40 is extracted therefrom. Fine probe 50 is next rotated by actuator $A_f$ to angular position 74 along the locus 52 whereat the second predetermined sample volume taken previously from open container $T_{o3}$ is disposed by fine probe 50 into an analysis device 70 located at the second dispensing position.

Example 4

Analytical Test 4 in which a liquid sample is extracted from a closed container and provided to a first analysis device after pretreatment and is also provided to a second analysis device before and after a diluting pretreatment.

1. Support 12 is rotated by actuator $A_s$ to position slot 16S6 containing closed container $T_{c6}$ at the first predetermined outer sample extracting position 18E. Gross probe 40 is rotated by actuator $A_g$ to position gross probe 40 at the first predetermined sample outer extracting position 18E. Gross probe 40 is operated to extract a first predetermined sample volume from closed container $T_{c6}$, is withdrawn from the sample liquid operated to extract a first volume of air and repositioned into the sample liquid to extract a second predetermined sample volume from closed container $T_{c6}$, operated to extract a second volume of air and repositioned to extract a third predetermined sample volume from closed container $T_{c6}$, the first and second volumes of air separating the first, second and third predetermined sample volumes.

2. Carrier 24 is rotated by actuator $A_c$ to position well 24W6 in the inner concentric annular array of wells 26A at the first predetermined inner operating position 28I. Gross probe 40 is next rotated by actuator $A_g$ to position gross probe 40 at the first predetermined inner operating position 28I whereat the third predetermined sample volume taken previously from closed container $T_{c6}$ is disposed into well 24W6.

3. Carrier 24 is rotated by actuator $A_c$ to position well 24W7 in the inner concentric annular array of wells 26A at the first predetermined inner operating position 28I. Gross probe 40 is next rotated by actuator $A_g$ to position gross probe 40 at the first predetermined inner operating position 28I whereat the second predetermined sample volume taken previously from closed container $T_{c6}$ is disposed into well 24W7.

4. Carrier 24 is rotated by actuator $A_c$ to position well 24W4 in the inner concentric annular array of wells 26A at the first predetermined inner operating position 28I. Gross probe 40 is next rotated by actuator $A_g$ to position gross probe 40 at the first predetermined inner operating position 28I whereat the first predetermined sample volume taken previously from closed container $T_{c6}$ is disposed into well 24W4.

5. Gross probe 40 is next rotated by actuator $A_g$ to position gross probe 40 at angular position 66 along the locus 42 whereat a wash solution is disposed in the second device 60. Gross probe 40 is operated to extract wash solution thereinto and subsequently to extract wash solution therefrom, a process that may be repeated sufficiently to cleanse gross probe 40.

6. Gross probe 40 is next rotated by actuator $A_g$ to position gross probe 40 at angular position 64 along the locus 42 whereat a dilution solution is disposed in the device 58. Gross probe is next operated to extract a predetermined volume of dilution solution therefrom. Gross probe 40 is next rotated by actuator $A_g$ to position gross probe 40 at the first predetermined inner operating position 28I whereat a first predetermined portion of dilution solution taken previously from device 58 is disposed into well 24W6 and whereat a second predetermined portion of dilution solution taken previously from device 58 is disposed into well 24W4.

7. Carrier 24 is next rotated by actuator $A_c$ to position well 24W6 in the inner concentric annular array of wells 26A at the second predetermined inner operating position 30I. Fine probe 50 is next rotated by actuator $A_f$ to position fine probe 50 at the second predetermined inner operating position 30I whereat the third predetermined sample volume taken previously from closed container $T_{c6}$ and disposed into well 24W6 by gross probe 40 is extracted therefrom. Fine probe 50 is next rotated by actuator $A_f$ to angular position 74 along the locus 52 whereat the third predetermined sample volume taken previously from closed container $T_{c6}$ is disposed by fine probe 50 into an analysis device 70 located at the second dispensing position.

8. Fine probe 50 is next rotated by actuator $A_f$ to position fine probe 50 at angular position 76 along the locus 52 whereat a wash solution is disposed in an additional device 72. Fine probe is operated to extract wash solution thereinto and subsequently to extract wash solution therefrom, a process that may be repeated sufficiently to cleanse fine probe 50.

9. Carrier 24 is next rotated by actuator $A_c$ to position well 24W7 in the inner concentric annular array of wells 26A at the second predetermined inner operating position 30I. Fine probe 50 is next rotated by actuator $A_f$ to position fine probe 50 at the second predetermined inner operating position 30I whereat the second predetermined sample volume taken previously from closed container $T_{c6}$ and the predetermined volume of dilution solution taken previously from device 58 and also disposed into well 24W7 is extracted therefrom. Fine probe 50 is next rotated by actuator $A_f$ to position fine probe 50 at the second dispensing position whereat the second predetermined sample volume taken previously from closed container $T_{c6}$ and the predetermined volume of dilution solution take previously from device 58 and also disposed into well 24W7 is disposed by fine probe 50 into an analysis device 70 located at the second dispensing position.

10. Carrier 24 is next rotated by actuator $A_c$ to position well 24W4 in the inner concentric annular array of wells 26A at the first predetermined inner operating position 30I. Gross probe 40 is next rotated by actuator $A_g$ to position gross probe 40 at the first predetermined inner operating position 28I whereat the predetermined portion of dilution solution taken previously from device 58 is disposed into well 24W4 and whereat the second predetermined portion of dilution solution taken previously from device 58 is disposed into well 24W4 are extracted therefrom. Gross probe 40 is next rotated by actuator $A_g$ to position gross probe 40 at the second dispensing position located at angular position 62 along the locus 42 whereat the first predetermined sample volume taken previously from closed container $T_{c6}$ and the second predetermined portion of dilution solution taken previously from device 58 are dispensed.

Example 5

Analytical Test 5 in which a first liquid sample is extracted from an open container and provided directly to a first analysis device without pretreatment and in which a second liquid sample is extracted from an open container and provided directly to a second analysis device without pretreatment.

1. Support 12 is rotated by actuator $A_s$ to position slot 16S4 containing open container $T_{o4}$ at the first predetermined inner sample extracting position 18I. Gross probe 40 is rotated by actuator $A_g$ to position gross probe 40 at the first predetermined inner extracting position 18I. Gross probe 40 is operated to extract a first predetermined sample volume from open container $T_{o4}$.

2. Gross probe 40 is next rotated by actuator $A_g$ to position gross probe 40 at the second dispensing position located at angular position 62 along the locus 42 whereat the first predetermined sample volume taken previously from open container $T_{o4}$ is disposed into an analysis instrument 56 located at the second dispensing position.

3. Support 12 is rotated by actuator $A_s$ to position slot 16S4 containing open container $T_{o4}$ at the second predetermined inner sample extracting position 20I. Fine probe 50 is rotated by actuator $A_f$ to position fine probe 50 at the second predetermined inner sample extracting position 20I and is operated to extract a second predetermined sample volume from open container $T_{o4}$. Fine probe 50 is next rotated by actuator $A_f$ to position fine probe 50 at the second predetermined dispensing position whereat the second predetermined sample volume previously taken from open container $T_{o4}$ is disposed by fine probe 50 into an analysis device 70 located at the second dispensing position.

Example 6

Analytical Test 6 in which liquid samples extracted from closed and open containers are provided to an analysis device(s) in a different sequence than that in which they were extracted from the containers without pretreatment.

1. Support 12 is rotated by actuator $A_s$ to position slot 16S1 containing closed container $T_{c1}$ at a first predetermined outer sample extracting position 18E. Gross probe 40 is rotated by actuator $A_g$ to position gross probe 40 at the first predetermined outer sample extracting position 18E and is operated to extract a first predetermined sample volume from closed container $T_{c1}$.

2. Carrier 24 is rotated by actuator $A_c$ to position well 24W1 in the inner concentric annular array of wells 26A at the first predetermined inner operating position 28I. Gross probe 40 is next rotated by actuator $A_g$ to position gross probe 40 at the first predetermined inner operating position 28I whereat the first predetermined sample volume taken previously from closed container $T_{c1}$ is disposed into well 24W1.

3. Support 12 is rotated by actuator $A_s$ to position slot 16S2 containing closed container $T_{c2}$ at a first predetermined inner sample extracting position 18I. Gross probe 40 is rotated by actuator $A_g$ to position gross probe 40 at the first predetermined inner extracting position 18I and is operated to extract a second predetermined sample volume from closed container $T_{c2}$.

4. Carrier 24 is rotated by actuator $A_c$ to position well 24W2 in the inner concentric annular array of wells 26A at the first predetermined inner operating position 28I. Gross probe 40 is next rotated by actuator $A_g$ to position gross probe 40 at the second predetermined inner operating position 28I whereat the second predetermined sample volume taken previously from closed container $T_{c2}$ is disposed into well 24W2.

5. Support 12 is rotated by actuator $A_s$ to position slot 16S3 containing open container $T_{o3}$ at a first predetermined outer sample extracting position 18E. Gross probe 40 is rotated by actuator $A_g$ to position gross probe 40 at the first predetermined outer sample extracting position 18E and is operated to extract a third predetermined sample volume from open container $T_{o3}$.

6. Carrier 24 is rotated by actuator $A_c$ to position well 24W3 in the outer concentric annular array of wells 26A at the first predetermined outer operating position 28E. Gross probe 40 is next rotated by actuator $A_g$ to position gross probe 40 at the first predetermined outer operating position 28E whereat the third predetermined sample volume taken previously from open container $T_{o3}$ is disposed into well 24W3.

7. Support 12 is rotated by actuator $A_s$ to position slot 16S4 containing open container $T_{o4}$ at a first predetermined inner sample extracting position 18I. Gross probe 40 is rotated by actuator $A_g$ to position gross probe 40 at the first predetermined inner extracting position 18I and is operated to extract a fourth predetermined sample volume from open container $T_{o4}$.

8. Carrier 24 is rotated by actuator $A_c$ to position well 24W4 in the inner concentric annular array of wells 24A at the first predetermined inner operating position 28I. Gross probe 40 is next rotated by actuator $A_g$ to position gross probe 40 at the first predetermined inner operating position 28I whereat the fourth predetermined sample volume taken previously from open container $T_{o4}$ is disposed into well 24W4.

9. Carrier 24 is next rotated by actuator $A_c$ to position well 24W2 in the inner concentric annular array of wells 26A at the second predetermined inner operating position 30I. Fine probe 50 is rotated by actuator $A_f$ to position fine probe 50 at the second predetermined inner operating position 30I whereat the second predetermined sample volume taken previously from closed container $T_{c2}$ and disposed into well 24W2 by gross probe 40 is extracted therefrom. Fine probe 50 is next rotated by actuator $A_f$ to angular position 74 along the locus 52 whereat the second predetermined sample volume taken previously from closed container $T_{c2}$ is disposed by fine probe 50 into an analysis device 70 located at the second dispensing position.

10. Carrier 24 is next rotated by actuator $A_c$ to position well 24W4 in the inner concentric annular array of wells 26A at the second predetermined inner operating position 30I. Fine probe 50 is rotated by actuator $A_f$ to position fine probe 50 at the second predetermined inner operating position 30I whereat the first predetermined sample volume taken previously from open container $T_{o4}$ and disposed into well 24W4 by gross probe 40 is extracted therefrom. Fine probe 50 is next rotated by actuator $A_f$ to angular position 74 along the locus 52 whereat the fourth predetermined sample volume taken previously from open container $T_{o4}$ is disposed by fine probe 50 into an analysis device 70 located at the second dispensing position.

11. Carrier 24 is next rotated by actuator $A_c$ to position well 24W1 in the inner concentric annular array of wells 26A at the second predetermined inner operating position 30I. Fine probe 50 is rotated by actuator $A_f$ to position fine probe 50 at the second predetermined inner operating position 30I whereat the first predetermined sample volume taken previously from closed container $T_{c1}$ and disposed into well 24W1 by gross probe 40 is extracted therefrom. Fine probe 50 is next rotated by actuator $A_f$ to angular position 74 along the locus 52 whereat the first predetermined sample volume taken previously from closed container $T_{c1}$ is disposed by fine probe 50 into an analysis device 70 located at the second dispensing position.

12. Carrier 24 is next rotated by actuator $A_c$ to position well 24W3 in the outer concentric annular array of wells 26B at the second predetermined outer operating position 30E. Fine probe 50 is rotated by actuator $A_f$ to position fine probe 50 at the second predetermined outer operating position 30E whereat the third predetermined sample volume taken previously from open container $T_{o3}$ and disposed into well 24W3 by gross probe 40 is extracted therefrom. Fine probe 50 is next rotated by actuator $A_f$ to angular position 74 along the locus 52 whereat the third predetermined sample volume taken previously from open container $T_{o3}$ is disposed by fine probe 50 into an analysis device 70 located at the second dispensing position.

Example 7

Analytical Test 7 in which a liquid sample is extracted from a closed container and provided to a second analysis device after a diluting pretreatment and after a chemical reagent pretreatment.

1. Support 12 is rotated by actuator $A_s$ to position slot 16S2 containing closed container $T_{c2}$ at the first predetermined inner sample extracting position 18I. Gross probe 40 is rotated by actuator $A_g$ to position gross probe 40 at the first predetermined inner sample extracting position 18I and is operated to extract a first predetermined sample volume from closed container $T_{c2}$.

2. Carrier 24 is rotated by actuator $A_c$ to position well 24W2 in the inner concentric annular array of wells 26A at the first predetermined inner operating position 28I. Gross probe 40 is next rotated by actuator $A_g$ to position gross probe 40 at the first predetermined inner operating position 28I whereat the first predetermined sample volume taken previously from closed container $T_{c1}$ is disposed into well 24W2.

3. Gross probe 40 is next rotated by actuator $A_g$ to position gross probe 40 at angular position 66 along the locus 42 whereat a wash solution is disposed in the second device 60. Gross probe 40 is operated to extract wash solution thereinto and subsequently to extract wash solution therefrom, a process that may be repeated sufficiently to cleanse gross probe 40.

4. Gross probe 40 is next rotated by actuator $A_g$ to position gross probe 40 at angular position 64 along the locus 42 whereat a dilution solution is disposed in the device 58. Gross probe 40 is next operated to extract a predetermined volume of dilution solution therefrom. Gross probe 40 is next rotated by actuator $A_g$ to position gross probe 40 at the first predetermined inner operating position 28I whereat the predetermined volume of dilution solution taken previously from device 58 is disposed into well 26W2.

5. Gross probe 40 is next rotated by acutator $A_g$ to position gross probe 40 at angular position 66 along the locus 42 whereat a wash solution is disposed in the second device 60. Gross probe 40 is operated to extract wash solution thereinto and subsequently to extract wash solution therefrom, a process that may be repeated sufficiently to cleanse gross probe 40.

6. Gross probe 40 is next rotated by actuator $A_g$ to position gross probe 40 at angular position 64A along the locus 42 whereat a chemical reagent solution is disposed in the device 58A. Gross probe is next operated to extract a predetermined volume of chemical reagent solution therefrom. Gross probe 40 is next rotated by actuator $A_g$ to position gross probe 40 at the first predetermined inner operating position 28I whereat the predetermined volume of chemical reagent taken previously from device 58A is disposed into well 24W2. At this point, if desired, a predetermined period of time may be allowed to elapse before the following step 7 is enacted.

7. Carrier 24 is next rotated by actuator $A_c$ to position well 24W2 in the inner concentric annular array of wells 26A at the second predetermined inner operating position 30I. Fine probe 50 is next rotated by actuator $A_f$ to position fine probe 50 at the second predetermined inner operating position 30I whereat the first predetermined sample volume taken previously from closed container $T_{c2}$ and the predetermined volume of dilution solution taken previously from device 58 and the predetermined volume of chemical reagent taken previously from device 58A and also disposed into well 24W2 is extracted therefrom. Fine probe 50 is next rotated by actuator $A_f$ to position fine probe 50 at the second dispensing position 74 whereat the first predetermined sample volume taken previously from closed container $T_{c2}$ and the predetermined volume of dilution solution taken previously from device 58 and the predetermined volume of chemical reagent taken previously from device 58A and also disposed into well 24W2 is disposed by fine probe 50 into an analysis device 70 located at the second dispensing position.

Those skilled in the art, having the benefit of the teachings of the present invention may effect numerous modifications thereo. Such modifications are to be construed as lying within the contemplation of the present invention, as defined by the appended claims.

What is claimed is:

1. An apparatus for extracting liquid from sample liquid containers and for dispensing liquid to at least two analyzers, the apparatus comprising:

a support for supporting sample containers, the support having an axis and being moveable with respect thereto;

a carrier having a plurality of receiving wells formed therein, the carrier having an axis and being moveable with respect thereto, the carrier axis and the support axis being displaced apart;

a gross probe moveable along a first locus of action and adapted to extract sample from the sample containers on said support and further adapted to dispense liquid into or extract liquid from said receiving wells;

a first chemical reservoir located along the first locus of action, the gross probe further adapted to extract liquid therefrom;

a first analysis device disposed along the first locus of action, the gross probe being further adapted to extract liquid from either of said sample containers or said receiving wells and dispense liquid into said first analysis device;

a fine probe moveable along a second locus of action, the fine probe adapted to extract liquid from the sample containers on said container support and further adapted to dispense liquid into said receiving wells;

a second chemical reservoir located along the second locus of action, the fine probe further adapted to extract liquid therefrom; and, a second analysis device disposed along the second locus of action, the fine probe being further adapted to extract liquid from either of said sample containers or said receiving wells and dispense liquid into said second analysis device.

2. The apparatus of claim 1 wherein the gross probe is able to extract and dispense relatively gross amounts of liquid.

3. The apparatus of claim 1 wherein the fine probe is able to extract and dispense relatively finely metered amounts of liquid.

4. The apparatus of claim 1 wherein the gross probe is able to withdraw liquid from either an open container or a closed container.

5. The apparatus of claim 1 wherein the fine probe is able to withdraw liquid from only an open container.

* * * * *